(12) United States Patent
Benum et al.

(10) Patent No.: US 10,105,658 B2
(45) Date of Patent: Oct. 23, 2018

(54) TRANSFER LINE

(71) Applicant: NOVA Chemicals (International) S.A., Fribourg (CH)

(72) Inventors: Leslie Wilfred Benum, Red Deer (CA); Michael Edward Koselek, Red Deer (CA); Vasily Simanzhenkov, Calgary (CA); Hany Iskandar Farag, Calgary (CA); Evan Geevouy Mah, Calgary (CA); Jeffrey Thomas Kluthe, Lacombe (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/491,479

(22) Filed: Apr. 19, 2017

(65) Prior Publication Data

US 2017/0312701 A1 Nov. 2, 2017

(30) Foreign Application Priority Data

May 2, 2016 (CA) ..................................... 2928459

(51) Int. Cl.
| | |
|---|---|
| *C10G 9/36* | (2006.01) |
| *F16L 9/02* | (2006.01) |
| *B01D 71/02* | (2006.01) |
| *B01D 53/22* | (2006.01) |
| *B01D 67/00* | (2006.01) |
| *C07C 5/327* | (2006.01) |
| *C07C 7/144* | (2006.01) |
| *B01J 8/00* | (2006.01) |
| *C01B 3/50* | (2006.01) |
| *C10G 9/00* | (2006.01) |

(52) U.S. Cl.
CPC ......... *B01D 71/025* (2013.01); *B01D 53/228* (2013.01); *B01D 67/0067* (2013.01); *B01D 71/02* (2013.01); *B01D 71/024* (2013.01); *B01J 8/009* (2013.01); *C01B 3/503* (2013.01); *C07C 5/327* (2013.01); *C07C 7/144* (2013.01); *C10G 9/002* (2013.01); *C10G 9/36* (2013.01); *F16L 9/02* (2013.01); *B01D 2053/221* (2013.01)

(58) Field of Classification Search
None
See application file for complete search history.

(56) References Cited

U.S. PATENT DOCUMENTS

| | | | |
|---|---|---|---|
| 4,078,292 A | | 3/1978 | Porter |
| 6,436,202 B1 | | 8/2002 | Benum et al. |
| 7,727,596 B2 | | 6/2010 | Ma et al. |
| 8,167,976 B2 | | 5/2012 | Del Paggio et al. |
| 8,791,037 B1 | | 7/2014 | Berchtold et al. |
| 9,273,805 B2 | | 3/2016 | Clavelle et al. |
| 2012/0251402 A1 | * | 10/2012 | Goto .................. B01D 46/2474 422/180 |
| 2013/0149223 A1 | * | 6/2013 | Blakeman ............ B01J 35/0006 423/213.5 |
| 2014/0178610 A1 | | 6/2014 | Clavelle et al. |
| 2015/0044130 A1 | | 2/2015 | Tang et al. |
| 2017/0100697 A1 | * | 4/2017 | Serra Alfaro ........ B01D 53/228 |
| 2018/0169634 A1 | * | 6/2018 | Patil ........................ B01J 29/40 |

* cited by examiner

*Primary Examiner* — Tam M Nguyen
(74) *Attorney, Agent, or Firm* — Julie Heinrich

(57) ABSTRACT

A transfer line between the outlet of a steam cracker and the inlet for the quench system has metallic or ceramic inserts having a pore size from about 0.001 to about 0.5 microns inside the line forming a gas tight barrier with the inner surface of the line and having a vent for the resulting gas tight pocket are used to separate $H_2$, $CH_4$, CO and $CO_2$ from cracked gases reducing the load on the down-stream separation train of the steam cracker.

20 Claims, No Drawings

TRANSFER LINE

The present disclosure relates to cracking paraffins, for example $C_{2-4}$ paraffins to olefins, including use of transfer line(s) between the outlet of a cracking furnace and the inlet for the quench system which is adapted to separate one or more of $H_2$, $CH_4$, CO, and $CO_2$ at temperatures from at least about 450° C., for example, from at least about 500° C., in some instances from about 700° C. to about 900° C. from the cracked gases.

In the back end of an ethylene steam cracker, a significant amount of capital equipment and energy is used to separate the components of a cracked gas to obtain relatively pure ethylene, from methane and other components including $H_2$, CO, and $CO_2$. If some or all of the $H_2$, $CH_4$, CO, and $CO_2$ could be separated from the cracked gases prior to entering the separation train, it would reduce the load on the separation train.

U.S. Pat. No. 4,078,292 issued Mar. 14, 1978 to Porter, assigned to Allied Chemical Corporation, teaches a method of repairing a cracked transfer line. The method involves cutting out the cracked portion of the transfer line and placing ceramics over the outside of the transfer line and then sealing the repaired transfer line in a metal sheath. The patent does not disclose that one or more of $H_2$, $CH_4$, CO, and $CO_2$ could be separated from the cracked gas via the ceramic.

The transfer line disclosed in the 292 patent is conical and this is generally the shape of transfer lines used today. However, published U.S. Patent Application Publication No. 2014/0178610 in the name of Clavelle et al., assigned to NOVA Chemicals (International) S.A, the text of which is herein incorporated by reference, teaches a transfer line (transfer line exchanger) with a non-uniform passage in which not less than 5% of the flow passage from the furnace outlet to the inlet to the quench system has an ARQ from 1.02 to 1.15. Rather than being conical, the transfer line looks like a thicker oval line which ends in a non-symmetrical bell shape. In some embodiments, the systems and methods disclosed herein would also be useful in such shaped transfer lines.

There are a series of patents in the name of Ma et al., assigned to the Worcester Polytechnic Institute, illustrated by U.S. Pat. No. 7,727,596 issued Jun. 1, 2010, that teach separating hydrogen from a gaseous mixture at temperatures up to about 500° C. The gas mixture appears to be predominantly $H_2$ and helium. There is no discussion of separating hydrogen from a gaseous mixture of hydrogen, $CH_4$, CO, $CO_2$ and olefins (ethylene). Interestingly, the patent discloses high temperature alloys having a pore size form 0.1 microns to 15 microns in some instances from 0.1 to 0.5 microns, which may be used as substrates for the separation membrane (Col. 7, lines 16-60).

U.S. Patent Application Publication No. 2015/0044130 published Feb. 12, 2015 in the name of Tang et al., assigned to Bettergy teaches doping zeolites with palladium to prepare a semi-permeable membrane useful at temperatures up to about 450° C. (see the tables in the examples). The tables in the examples show a high selectivity for hydrogen over molecules such as $CO_2$, and $CH_4$ at temperatures up to about 450° C. The specification does not teach or suggest the membranes would be useful at temperatures above 450° C.

U.S. Pat. No. 8,791,037 issued Jul. 29, 2014 to Berchtold et al., assigned to the U.S. Department of Energy, discloses a non oxide (Si/C/N) ceramic membrane stable at temperatures up to about 1000° C. The specification teaches the pore size may be controlled by monomer composition, comonomer functionality, photopolymerization conditions and pyrolysis conditions (Col. 6, lines 40-50). However, no details of the conditions are disclosed in the patent.

In some embodiments, the present disclosure seeks to provide a method to separate one or more of $H_2$, $CH_4$, CO, and $CO_2$ from a stream of cracked gases leaving a steam cracker prior to entering the quench system.

In one embodiment provided herein, is a transfer line between the outlet of a steam cracker and the inlet to a quench exchanger comprising:

i) a continuous passageway of a metal having a melting temperature greater than 1000° C. having a flange at one end of the passageway adapted to cooperate with the outlet from a steam cracking furnace and a flange at the opposite end of the passageway adapted to cooperate with the inlet to a quench exchanger; one or more inserts in said passageway permitting the flow of gases through said passageway, said inserts being permeable to at least one of $H_2$, $CH_4$, CO, and $CO_2$ at temperatures from 500° C. to 900° C. and spaced from the interior wall of the passageway and sealed to the interior wall of said passageway to provide one or more gas tight chambers; and one or more ports through the metal to withdraw gases from said one or more gas tight chambers;

said inserts being selected from:

a) ceramic inserts having a melting point greater than 900° C. and a porosity from 5 to 75% of pores having a size from 0.001 microns to about 5 microns, for example from 0.01 to 0.5 microns and fitting within the metal casting and b) metal inserts having a porosity from 5 to 75% of pores having a size from 0.001 microns to about 5 microns for example from 0.01 to 0.5 microns;

c) or both; and optionally ii) a membrane permeable to at least one of $H_2$, $CH_4$, CO, and $CO_2$ at temperatures from 500° C. to 900° C. on elements a), b) or both to permit the passage of at least one of $H_2$, $CH_4$, CO, and $CO_2$ there through into the gas tight chamber.

In a further embodiment, the insert is a porous ceramic formed from oxides, dioxides, nitrides, carbides and phosphates selected from porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

In a further embodiment, the ceramic insert is resistant to coking.

In a further embodiment, the ceramic insert is in the shape of a cone or an island.

In a further embodiment, the insert is a metal alloy comprising one or more of iron, nickel, titanium, chromium, aluminum, and molybdenum.

In a further embodiment, the metal insert is resistant to coking.

In a further embodiment, the metal insert is in the shape of a cone or an island. In a further embodiment, the membrane is present and has a thickness from 0.1 to 10 microns.

In a further embodiment, the membrane comprises one or more metals selected from Pd, Ta, V, Pt, Nb, and Zr.

In a further embodiment, the membrane further comprises one or more metal oxide ceramic selected from $Al_2O_3$, $BaTiO_3$, $SrTiO_3$ and $ZrO_2$.

In a further embodiment, the membrane is a dense metal oxide membrane.

In a further embodiment, in the membrane the metal comprises Pd.

In a further embodiment, the metal oxide comprises yttria stabilized $ZrO_2$

In a further embodiment, the metal oxide comprises calcia stabilized $ZrO_2$

In a further embodiment, the membrane is not less than about 95% of theoretical density.

In a further embodiment, the membrane is coated on component a).

In a further embodiment, a) comprises an alumina ceramic.

In a further embodiment, the membrane is coated on component b).

In a further embodiment, intermediate the ceramic oxide and component b) is a ceramic comprising one or more particles selected from tungsten, alumina oxide, zirconia, titania, silicon carbide, chromium oxide, yttrium oxide, having a particles size from 0.01 to 5 microns.

In a further embodiment, the membrane is Si/C/N ceramic formed by: combining a monomeric and/or oligomeric silazane ceramic precursor with a comonomer comprising one or more of the group consisting of ene (vinyl) functionalized, oligomeric, inorganic or organic silazanes, difunctional thiols, and tetrafunctional thiols;
   forming the combination as a thin film on a substrate;
   photopolymerizing the thin film; and
pyrolyzing the photopolymerized thin film so as to result in a ceramic membrane that contains substantially no oxide.

In a further embodiment, said monomeric and/or oligomeric silazanes contain heteroatoms selected from boron, titanium, aluminum, phosphorus, and combinations thereof.

In a further embodiment, provided herein is a method to remove one or more of $H_2$, $CH_4$, CO, and $CO_2$ from cracked gases leaving a cracking furnace by passing the gases through a transfer line as above at temperatures from 500° C. to 900° C.

In a further embodiment, provided here in is a cracking furnace and quench system for cracked gases comprising intermediate the exit of the cracking furnace and the quench system a transfer line as above.

Numbers Ranges:

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

In steam cracking of paraffins such as naphtha and lower alkanes such as $C_{2-4}$ paraffins, the feed together with steam is fed into tubes or coils passing through a convection section of the cracker where the feed is heated to close to cracking temperatures (about 750° C.). The feed then passes through coils in the radiant section of the furnace in a time from about 0.001 to 2.0 seconds, in some embodiments, from 0.001 to 1 second. In the radiant section of the furnace, wall mounted burners and or floor mounted burners heat the walls to a temperature where they radiate heat onto the coil surfaces. The temperature of the coil is in the range from about 800° C. to about 975° C. At these temperatures, the molecules are cracked, for example ethane is converted into ethylene. The composition of the gases leaving the furnace contain many species including free radicals and need to be quenched quickly to prevent further rearrangement of the molecules in the stream. The cracked gas stream passes through a transfer line to a heat exchanger where the gas is quickly quenched to a temperature to prevent any significant rearrangement of the molecules in the gas. The quenched gas then enters a separation train. In the separation train, the gas is sequentially cooled to low temperatures to condense methane, ethane and propane, and raffinates and other co-products. The co-products may include acetylene and other heavier products such as benzene, toluene and xylene (BTX). The product stream from the cracker also contains hydrogen, methane, carbon monoxide and carbon dioxide. These components also are cooled and passed through parts of the separation train. This puts an extra load on the separation train. In some embodiments, it is desirable to reduce the amount of $H_2$, $CH_4$, CO and $CO_2$ in the cracked gases prior to entering the separation train.

In accordance with the present disclosure, there is provided a transfer line between the outlet of a steam cracker and the inlet to a heat exchanger (quench system) comprising a continuous passageway of a metal having a melting temperature greater than 1000° C. having a flange at one end of the passageway adapted to cooperate with the outlet from a steam cracking furnace and a flange at the opposite end of the passageway adapted to cooperate with the inlet of a tube and shell heat exchanger or a quench system; one or more inserts in said passageway permitting the flow of gases through said passageway said inserts being permeable to at least one of $H_2$, $CH_4$, CO, and $CO_2$ at temperatures from 500° C., for example, from 550° C. to 900° C. being spaced from the interior wall of the passageway and sealed to the interior wall of said passageway to provide one or more gas tight chambers; and one or more ports through the metal to withdraw gases from said one or more gas tight chambers. In some embodiments it is desirable to minimize the diffusion of ethane and ethylene through the membranes to as low as possible. In some instances, the concentration of ethane and ethylene in the permeate stream should be less than 10 wt %, for example less than 5 wt. %, or for example less than 2 wt %, or for example less than 1 wt %, or in another example less than 0.5 wt. %.

The transfer line is typically cast from a metal having a melting point greater than 1000° C., for example greater than 1100° C. The transfer line may be made of any high temperature steel. In some embodiments, the transfer line is a stainless steel which may be selected from wrought stainless, austentic stainless steel and HP, HT, HU, HW and HX stainless steel, heat resistant steel, and nickel based alloys. The transfer line may be a high strength low alloy steel (HSLA); high strength structural steel or ultra-high strength steel. The classification and composition of such steels are known to those skilled in the art.

Further examples of suitable metal components include, but are not limited to, iron, nickel, titanium, chromium, aluminum, and alloys thereof, e.g., steel, stainless steel, HASTELLOY® alloys (e.g., HASTELLOY® C-22®) (trademarks of Haynes International, Inc., Kokomo, Ind.) and INCONEL® alloys (e.g., INCONEL® alloy 625) (INCONEL is a trademark of Huntington Alloys Corp., Huntington W. Va.). In one embodiment, the transfer line includes an alloy containing chromium and nickel (e.g., INCONEL® alloy 625). In an additional embodiment, the alloy contains chromium, nickel and molybdenum such as, for example, HASTELLOY® C-22® or INCONEL® alloy 625.

In one embodiment, the stainless steel, for example heat resistant stainless steel, comprises, for example, from 13 to 50, or for example, 20 to 50, or for example, from 20 to 38 weight % of chromium. The stainless steel may further comprise from 20 to 50, for example from 25 to 50, or for example, from 25 to 48, for example from about 30 to 45 weight % of Ni. The balance of the stainless steel may be substantially iron.

In some embodiments, the steel may further comprise a number of trace elements including at least 0.2 weight %, up to 3 weight %, for example, 1.0 weight %, up to 2.5 weight % or for example not more than 2 weight % of manganese; from 0.3 to 2, or, for example, 0.8 to 1.6, or less than 1.9 weight % of Si; less than 3, or less than 2 weight % of titanium, niobium (for example less than 2.0, or for example less than 1.5 weight % of niobium) and all other trace metals; and carbon in an amount of less than 2.0 weight %. The trace elements are present in amounts so that the composition of the steel totals 100 weight %.

In one embodiment, the stainless steel, for example heat resistant stainless steel comprises from 13 to 50, or for example 20 to 50, or for example from 20 to 38 weight % of chromium. The stainless steel may further comprise from 20 to 50, or for example from 25 to 50 or for example from 25 to 48, or for example from about 30 to 45 weight % of Ni. The balance of the stainless steel may be substantially iron.

Some embodiments of the disclosure may also be used with nickel and/or cobalt based extreme austenic high temperature alloys (HTAs). In some embodiments, the alloys comprise a major amount of nickel or cobalt. In some embodiments, the high temperature nickel based alloys comprise from about 50 to 70, or for example from about 55 to 65 weight % of Ni; from about 20 to 10 weight % of Cr; from about 20 to 10 weight % of Co; and from about 5 to 9 weight % of Fe and the balance one or more of the trace elements noted below to bring the composition up to 100 weight %. In some embodiments, the high temperature cobalt based alloys comprise from 40 to 65 weight % of Co; from 15 to 20 weight % of Cr; from 20 to 13 weight % of Ni; less than 4 weight % of Fe and the balance one or more trace elements as set out below and up to 20 weight % of W. The sum of the components adding up to 100 weight %.

In some embodiments, the steel may further comprise a number of trace elements including at least 0.2 weight %, up to 3 weight % or for example 1.0 weight %, up to 2.5 weight % or in another example not more than 2 weight % of manganese; from 0.3 to 2, or for example 0.8 to 1.6 or in another example less than 1.9 weight % of Si; less than 3, or less than 2 weight % of titanium, niobium (for example less than 2.0, or less than 1.5 weight % of niobium) and all other trace metals; and carbon in an amount of less than 2.0 weight %. The trace elements are present in amounts so that the composition of the steel totals 100 weight %.

Some embodiments of the disclosure are used with a transfer line having a good resistance to coke make, for example such as those disclosed in U.S. Pat. No. 6,436,202 issued Aug. 20, 2002 to Benum et al., assigned to NOVA Chemicals (International) S.A. In some embodiments, the run time between decoking the transfer line should be greater than 90 days, for example greater than 180 days or for example greater than 200 days.

The transfer line is, in some embodiments, cast as a single piece having a continuous impermeable wall to the gases separated from the cracked gas stream. In some instances, the transfer line could be cast as parts or portions of the line particularly where the line is as disclosed in U.S. Pat. No. 9,273,805 issued Jun. 26, 2014 to Clavelle et al., assigned to NOVA Chemicals (International) S.A.

In some embodiments, the transfer line could be conical, cast in two longitudinal half sections to be joined together. The joint needs to be gas tight.

Inside at least a portion of the transfer line are one or more inserts permeable to the passage of at least one of $H_2$, $CH_4$, CO, and $CO_2$ there through at temperatures from 500° C., for example from 550° C. to 900° C. in the passageway, not substantially blocking or obstructing the passage way, permitting the flow of gases through the passageway the inserts being spaced from the interior wall of the passageway and sealed to the interior wall of said passageway to provide one or more gas tight chambers. Not substantially blocking or obstructing the passage way means not blocking the passageway by more than 15%, in some embodiments less than 10%, in further embodiments less than 5% (e.g., by cross section of the passage). The insert could be a cast conical insert having a central passage way there through. In which case, the entire conical insert would be permeable to one or more of $H_2$, $CH_4$, CO, and $CO_2$. The insert could be a deformed cone as in the outlet of the transfer line disclosed in U.S. Pat. No. 9,273,805 having a central passage way there through. In some embodiments, the insert need not be cone shaped but would provide a round or elliptical "island" on the side of the interior wall of the transfer line. In some embodiments, when such "islands" are used, they are spaced so that there is still an open flow passage through the transfer line. The inserts are joined to the interior wall of the transfer line to provide a gas tight seal.

In some embodiments, the inserts may be ceramic. In some embodiments, the ceramic is stable at temperatures not less than 450° C. or for example not less than 500° C., or in some embodiments not less than 550° C., or in another example from 850° C. to 900° C. or in yet another example up to 1000° C. The ceramic should be porous ceramic formed from oxides, dioxides, nitrides, carbides and phosphates selected from porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof. In some embodiments, the ceramic membrane may be a dense gas-selective membrane as described below.

Exemplary components for forming ceramic membranes include oxides of titanium, zirconium, aluminum (e.g., alpha alumina and gamma alumina), magnesium, silicon and mixtures thereof. Ceramics of mixed alumina and silicon oxide are zeolites and the titanium equivalents are ETS type ceramics. The pore size in the structure of the ceramic material may be from 0.001 to 1 micron in some embodiments from 0.01 to 0.5 microns. This pore size is sufficient to permit one or more of $H_2$, $CH_4$, CO and $CO_2$ to diffuse or permeate through the ceramic. However, it should be noted the ceramic need not necessarily be compacted to exclude interstitial spaces, so that the gases extracted from the cracked gas stream could also pass through the interstitial spaces in the cast ceramic.

In some embodiments, the ceramic may be doped with or contain, particles, fibers or whisker of a metal that helps transport one or more of hydrogen, methane, carbon monoxide and carbon dioxide. Palladium, niobium, tantalum, zirconium, vanadium and alloys thereof may be used for these purposes.

The pore size of the ceramic must be large enough to permit a molecule selected from hydrogen, methane, carbon monoxide and carbon dioxide to pass through the ceramic particles. The internal pore sized of the ceramic particles may range from 0.0003 to 1.0 microns or larger.

In some embodiments, the ceramic inserts may have a non-coking or low coking surface such as a sodium aluminum complex.

The inserts may also be a metal or alloy having a melting point above 450° C., or for example above 500° C. or for example above 900° C., or for example above 1000° C., or in another example above 1050° C. The porous metal can be formed from any of a variety of components known to those of ordinary skill in the art. Examples of suitable metal or alloy components include, but are not limited to, iron, nickel, titanium, chromium, aluminum, and alloys thereof, e.g., steel, stainless steel, HASTELLOY® alloys (e.g., HASTELLOY® C-22®) (trademarks of Haynes International, Inc., Kokomo, Ind.) and INCONEL® alloys (e.g., INCONEL® alloy 625) (INCONEL is a trademark of Huntington Alloys Corp., Huntington W. Va.). In one embodiment, the porous substrate includes an alloy containing chromium and nickel (e.g., INCONEL® alloy 625). In an additional embodiment, the alloy contains chromium, nickel and molybdenum such as, for example, HASTELLOY® C-22® or INCONEL® alloy 625. The porous metal can be porous stainless steel. Porous stainless steel that is suitable for use as substrates are available from Mott Metallurgical Corporation (Farmington, Conn.) and from Pall Corporation (East Hills, N.Y.), for example.

One of ordinary skill in the art can select substrate thickness, porosity, and pore size distribution using techniques known in the art. Desired substrate thickness, porosity and pore size distribution can be selected based on, among other factors, the operating conditions of the final composite gas separation module such as operating pressure. Substrates having generally higher porosities and generally smaller pore sizes are particularly suited for producing composite gas separation modules. In some embodiments, the substrate can have a porosity in a range of about 5 to about 75% or about 15 to about 50%. While the pore size distribution of a substrate can vary, the substrate can have pore diameters that range from about 0.001 microns or less to about 15 microns or for example from 0.01 to 5 microns, or in another example from 0.1 to 0.5 microns.

In some embodiments, smaller pore sizes are preferred. However, in some embodiments, a substrate having larger pores is used and an intermediate layer having generally smaller pore sizes is formed on the porous substrate (e.g., a graded support is formed).

In some embodiments, the mean or median pore size of the substrate can range from about 0.001 to about 15 microns, e.g., from about 0.01 micron to about 1, 3, 5, 7 or about 10 microns. For example, the substrate can be an about 0.1 micron grade substrate to an about 0.5 micron grade substrate, e.g., 0.01 micron, 0.2 micron, and 0.5 micron grades of stainless steel substrates can be used.

Both the ceramic and metallic inserts may optionally be coated with a gas-selective membrane.

In one embodiment, the gas selective membrane is a dense gas-selective membrane selectively permeable to hydrogen, and can include one or more hydrogen-selective metals or alloys thereof. Hydrogen-selective metals include, but are not limited to, niobium (Nb), tantalum (Ta), vanadium (V), palladium (Pd), platinum (Pt), zirconium (Zr) and hydrogen-selective alloys thereof. In some embodiments, palladium and alloys of palladium are preferred. For example, palladium can be alloyed with at least one of the metals selected from gold, platinum, ruthenium, rhodium, yttrium, cerium and indium. Some care needs to be exercised in selecting components to use in the alloys. Copper and silver have been suggested as alloy components. However, as cracked gas may contain acetylene and steam one would avoid silver and copper as alloy components as there may be a tendency to form silver of copper acetylide which present an explosive hazard. The metallic component may have a particle size from about 0.3 to about 3 microns.

The dense gas-separation membrane can include one or more components that are not gas-selective materials, e.g., components that are not hydrogen-selective materials such as metal oxide ceramics. Examples of some useful metal oxide ceramics are alumina ($Al_2O_3$), barium titanate (Ba-$TiO_3$), strontium titanate ($StTiO_3$), zirconia $ZrO_2$) stabilized or partially stabilized with yttria or calcia and various combinations thereof. When used, the metal oxide ceramic may be present in an amount of from 10 to 90 wt. %, or from 30 to 70 wt. % or for example from 40 wt. % to 60 wt. % of the blend of the metal and metal oxide ceramic.

The dense gas-selective membrane may have a thickness from about 0.1 to 10 microns. For example, in one embodiment, the thickness of the dense gas-selective membrane is less than about 10 microns such as about 3 to 8 microns, in some embodiments less than 0.5 microns. In some embodiments the membrane is a uniform thickness which means the thickness across the membrane may vary by about +/−1 micron, or less than about +/−1 micron.

In some embodiments the metal components for the dense gas—selective membrane are activated by bringing them into contact with a solution of $SnCl_2$ (e.g., 1 g/l pH approximately 2) then filtering the powder from the solution shortly after contact and washing it and optionally drying it to obtain the activated metal ($PdCl_2$). The activated metal together with the metal oxide ceramic, if present, may be used as a powder or dispersed (slurry) or re-dissolved in a suitable solvent or diluent (e.g., water).

A layer of particulate material to form the dense gas phase selective membrane is brought into contact with the upper or outer surface of the porous ceramic or metal inserts (relative to the flow path of the cracked gas) by any suitable method known to those skilled in the art for applying a particulate material (e.g., powder) to a porous surface. For example, the particulate material may be applied to the surface of the porous insert by transport with a gas, or by application of a paste, a slurry or suspension of the particulate material, or by pressing or rubbing a powder of the particulate materials upon the surface of the porous insert.

In one embodiment, at least one of the contacting steps is conducted while applying a pressure differential of a higher pressure and a lower pressure across the insert with the higher pressure being applied to the side of the upper or outer surface of the insert. The application of the pressure differential can be accomplished through use of a negative pressure (i.e., vacuum applied to the other (e.g., lower or inner) surface of the insert, or a positive pressure (i.e., pressure applied to the outer surface of the insert), or a combination of the two. In some embodiments, the particulate material is deposited as a slurry under the application of a vacuum to the second (i.e., inner) surface of the porous insert.

The quantity and size of particulate material applied to the upper or outer surface of the porous insert (relative to the flow path of the cracked gas) can vary somewhat depending on the method utilized to deposit the particulate material. The primary goal in the application of particulate material is to completely cover the surface of the porous insert that will ultimately support the dense gas selective (separation) membrane.

After the particulate material is placed in contact with the upper or outer surface of the porous insert to form a first coated surface any excess first particulate material that is present on the insert is removed. The method of removal may vary depending upon the method of application but in most instances it may be removed by friction (e.g., mechanical or hand rubbing). In some embodiments, the step of removing the excess particulate material is conducted while a vacuum is applied to the lower or inner surface of the insert (the surface opposite the applied particulate material). If the particulate material was deposited using a wet process (e.g., slurry or suspension), the coated insert should be dried prior to removing the excess particulate material to avoid removing slabs of wet particulate cake which may pull particulate material from the pores of the porous insert.

In some embodiments, the application of the particulate material (metallic components of a smaller particles size having an average particle diameter ranging, e.g., from about 0.001 to about 1 micron) may be conducted to reduce the mean pore size of resulting coated porous support and to reduce the surface roughness of the porous support. Achieving these goals involves addressing several variables in the selection of the particulate material (e.g., choice of particulate material, method of application, particle size, etc.)

The deposition of the dense phase gas-selective membrane may be carried out in one step or in multiple steps, and in some embodiments, with annealing after each step.

One useful method for annealing involves heat treating the coated porous substrate in an inert atmosphere at lower temperatures and thereafter in the presence of hydrogen. More specifically, the annealing takes place in the absence of hydrogen until the annealing temperature is at least 250° C., or at least 300° C., or for example, at least 350° C. Once the annealing temperature reaches 250° C., or for example 300° C., or for example 350° C., hydrogen and oxygen can be present in the annealing step. Stated alternatively, in some embodiments, the annealing step is conducted in a hydrogen containing atmosphere after the temperature has reached a minimum of 300° C., for example at least 350° C. or for example at least 400° C. Although the annealing step can be taken to very high temperatures (e.g., 600° C. or greater), in most instances, the annealing step occurs at temperatures between 350° C. and 550° C., or for example between 400° C. and 500° C. In embodiments where the membrane is built up by successive coatings, hydrogen is purged from the system as the membrane cools between deposition steps. In some embodiments, hydrogen is purged by flooding the system with an inert gas as the membrane starts to cool so that no hydrogen is present as the membrane reaches 300° C., for example, 400° C.

Inert gases that may be used in this heat treatment step include nitrogen, helium, argon, neon and carbon dioxide. The inert gas for use in the annealing step may be selected from nitrogen, argon, neon and carbon dioxide. In one embodiment, the inert gas for use in the heat treatment is nitrogen.

The gaseous atmosphere under which the annealing step is conducted should have some hydrogen in it once the annealing temperature reaches at least 300° C., or in some embodiments greater than 300° C. The gaseous atmosphere used during the annealing step of the plated porous substrate should comprise a mixture of hydrogen from 3 to 100% and inert gas from 97 to 0%.

The annealing is conducted at a temperature that sufficiently treats the thin layer of gas-selective material (metal) that overlies the outer surface of the porous insert. While the required annealing temperature depends somewhat upon the particular metal or metal alloy that is plated upon the porous insert and the thickness of the layer thereof. In some embodiments, the heat treatment temperature should be in the range of from at least 300° C. to 800° C. In some embodiments, the heat treatment temperature is in the range of from 325° C. to 700° C., or, in another example, the heat treatment temperature is in the range of from 350° C. to 550° C.

The annealing step is conducted for a period of time sufficient to provide the necessary treatment of the layer of gas-selective material and where required prepare it for the next series of plating, polishing and annealing. The annealing time period may, thus, be in the range upwardly to 48 or more hours, but, a typical annealing time period is in the range of from 0.1 hours to 12 hours. In some embodiments, annealing time is minimized to such a time necessary to provide the treatment of the layer of gas-selective metal required to achieve the benefits described herein. It is expected that such a time period is in the range of from 0.2 to 10 hours, or even in the range of from 0.3 hours to 4 hours.

The pressure under which the annealing is conducted can be in the range of from 0.5 atmospheres (absolute) to 20 atmospheres. In some embodiments, the heat treatment pressure is in the range of from 0.8 atm. to 10 atm.

It is believed that the grain growth parameters of the deposited metal increases membrane stability and helps it resist change at elevated temperatures. Encouraging grain growth by increasing the annealing temperature appears to have a beneficial effect, particularly when the layers of gas selective material are polished between deposition steps. The polishing step is discussed in more detail below. It is thought that there is some positive effect in polishing the grains to effectively smear them into the open pores and form a uniform metal layer. Gas separation systems formed in such a manner have been observed to resist cracking at high operational temperatures.

After annealing, the porous insert with its annealed supported membrane layer is polished/abraded. The polishing improves the surface of the deposited layer for further deposition by minimizing surface abnormalities and deformities and by filling openings such as cracks, pinholes and other imperfections that may be present in the thin membrane layer. Exemplary abrading and polishing methods are disclosed in U.S. Pat. No. 8,167,976 issued May 1, 2012 in the name of Del Paggio et al., assigned to Shell Oil Company.

In a further embodiment, the gas selective membrane is formed from an inorganic polymeric precursor which is crosslinked by photo initiation and then pyrolysed.

In some embodiments, the method involves pyrolyzing the photo-polymerized thin film so as to result in a ceramic membrane that contains substantially no oxide. "Substantially no oxide" means less than 5 wt. % oxide, or in some embodiments less than 2 wt. % oxide, or in further embodiments less than 0.5 wt. % oxide.

The materials further usefully employed fall into two categories: the monomeric or oligomeric ceramic precursors and the multifunctional thiol monomers. The ceramic precursors of primary interest are vinyl functionalized, inorganic-organic silazanes. The composition and functionality of the thiolated comonomer is another variable that can be used to control the crosslinked polymer product properties. Non-oxygen containing alkane dithiols with varying chain lengths and tetrathiols both independently and in tandem are preferred in some embodiments.

Comonomer concentration (silazane/thiol), comonomer functionality (e.g., dithiol vs tetrathiol and the ratio of the two when used in tandem), and dithiol chain length are system variables that allow for controlled manipulation of the polymerization kinetics, network formation characteristics, and correspondingly, the final properties of the polymer product.

Polymer films should be formed utilizing the photo-induced free-radical step-growth thiol-ene polymerization disclosed herein where the "ene" functionality is incorporated via the silazane ceramic precursor. In some embodiments, polymerization is conducted on bulk materials, i.e., no solvent is needed. In some embodiments, the common UV photoinitiator, 2,2-dimethoxy-2-phenylacetophenone, can be used to adjust the initiation kinetics. A unique feature of these thiol-ene reactions is their ability to self-initiate; therefore, the use of a separate photoinitiator is optional, providing an additional level of control over the molecular composition and homogeneity of the polymer product.

The polymer material properties are intimately linked to the properties of the monomeric/oligomeric reactants, the polymerization mechanism utilized, the reaction conditions (temperature, atmosphere, initiation rate (irradiation intensity, initiator concentration, and self-initiating monomer concentration, and initiation wavelength(s))), and the extent of conversion of the reactive functionalities. All of these factors cumulatively dictate the polymerization kinetics and, correspondingly, the material and chemical properties of the polymer product and thus, its separation characteristics.

Formation of an amorphous ceramic membrane may be accomplished by heating and pyrolysis of the polymeric ceramic precursor fabricated via the step-growth photo-polymerization described previously. Just as the polymer fabrication conditions and kinetics play a large role in property determination, so do pyrolysis conditions and kinetics. Thus, an understanding of the dependence of the polymer/ceramic structure/properties on the material's thermal history is essential, in some embodiments.

In some embodiments, pyrolysis of the crosslinked polymeric ceramic precursors is conducted in several different atmospheres, namely, under air, vacuum, nitrogen, argon, and ammonia, where the atmosphere dictates the pyrolysis chemistry and thus, relative Si—C—N compositions in the final product with attainable compositions ranging from pure SiC to pure $Si_3N_4$. The heating rate, ultimate temperature, soak time at temperature, and cooling rate are also used, in some embodiments, to control the polymer to amorphous ceramic transition and thus, the product properties.

The systems and methods disclosed herein are, in some preferred embodiments, relevant to hydrogen separation. A recurring theme in the production of hydrogen is the separation of hydrogen from carbon dioxide or carbon monoxide and other minority components. There are a number of processes where it would be advantageous to perform the separation using membranes at elevated temperatures. For example, in a water-gas-shift reactor, removing the hydrogen at the temperature of reaction (200 to 700° C.) would improve the efficiency of the process. The disclosure provides robust ceramic membranes that will selectively transport hydrogen at up to 1000° C. and higher. This novel route utilizes preceramic polymeric precursors which gives one the ability to use established and economical polymer membrane fabrication techniques.

Some embodiments disclosed herein also address the long-standing issue of ceramic durability. Some bulk engineering ceramics prepared using embodiments disclosed herein have proven to be much more robust than traditional ceramics. This result is due, at least in part, to the final composition of the ceramic, which is not obtained using standard ceramic fabrication techniques In some embodiments, the gas-selective membrane may overlie an intermediate layer between the membrane and the substrate.

The intermediate layer includes particles and a binder metal. The binder metal is uniformly distributed throughout the intermediate layer. The term "uniformly distributed," as used herein, refers to a uniform distribution of binder metal across the surface area of the particles of the intermediate layer. In one embodiment, the binder metal is a hydrogen-selective metal or an alloy thereof. "Hydrogen-selective metals" include, but are not limited to, niobium (Nb), tantalum (Ta), vanadium (V), palladium (Pd), platinum (Pt), zirconium (Zr) and hydrogen-selective alloys thereof. In some embodiments, palladium and alloys of palladium are preferred.

In some embodiments, the intermediate layer includes particles uniform in size, e.g., of uniform diameter. Alternatively, the intermediate layer can include particles of varying sizes and/or size distributions. The intermediate layer can include blends and/or layering of different particles including particles of differing sizes. The intermediate layer can include a gradient of particle size from a surface of the intermediate layer proximate to the porous substrate (insert) to a surface of the intermediate layer distal to the porous substrate (insert). In one embodiment, particles having a smaller average size overlie particles having a larger average size. For example, particles having a larger average size are located proximate to the porous substrate (e.g., inside the pores of the porous substrate) and particles having a smaller average size are located distal to the porous substrate (e.g., inside the pores of the porous substrate but closer to the membrane-side surface of the porous substrate).

In one embodiment, the particles can have an average particle diameter of at least about 0.01 micron such as at least about 0.1, 0.5, 1, or at least about 5 microns. The particles can include particles capable of fitting into pores of the porous substrate. In some embodiments, the particles can have an average particle diameter of less than 5 microns such as less than 1, 0.5, 0.1, or less than 0.01 microns. In one embodiment, the particles have an average diameter ranging from about 0.01 to about 5 microns. For example, the particles can have an average diameter ranging from about 0.01 to about 3 microns or about 0.3 to about 1 micron.

In one embodiment, the intermediate layer includes sublayers of particles and binder metal, e.g., at least two sublayers of particles and binder metal. For example, the sublayers of particles and binder metal can include a first sublayer of a first population of particles and a first binder metal and a second sublayer of a second population of particles and a second binder metal, wherein the first population of particles has a larger average diameter than the average diameter of the second population of particles and wherein the second sublayer overlies the first sublayer. Thus, in one embodiment, the intermediate layer includes a sublayer of particles having a larger average diameter and an overlying sublayer of particles having a smaller average diameter. For example, the intermediate layer can include a sublayer of particles having an average diameter of about 0.3 to about 3 microns and an overlying sublayer of particles having an average diameter of about 0.1 to about 1 micron. Sublayers of particles and binder metal are not necessarily distinct sublayers. For example, the intermediate layer can include a gradient of particle sizes in a binder metal. In one embodiment, the intermediate layer includes a gradient of particle sizes ranging from generally larger particles at a point proximate to the porous substrate to generally smaller particles at a point distal to the porous substrate.

The particles of the intermediate layer can include metal particles, metal oxide particles, ceramic particles, zeolite particles, and combinations thereof, among others. For example, the particles can include such materials as tungsten, aluminum oxide, zirconia, titania, silicon carbide, chromium oxide, and combinations thereof. Suitable metal oxide particles include, but are not limited to, aluminum oxide, titanium oxide, yttrium oxide, and chromium oxide. In some embodiments, the particles include aluminum oxide particles, e.g., alpha-alumina particles and/or gamma-alumina particles. The particles can include a blend or a layering of different particles including particles of differing compositions and/or sizes. The particles of the intermediate layer can have various morphologies and shapes. For example, the particles can be ordered (e.g., crystalline) or amorphorus. In one embodiment, the particles include spherical or mostly spherical particles.

In some embodiments, the particles can have a melting point higher than the melting point of the porous substrate (insert), e.g., a porous metal substrate. The intermediate layer can include particles having a melting point higher than the melting point of the dense gas-selective membrane. For example, in one embodiment, the intermediate layer includes particles having a melting point temperature higher than both the melting point temperature of the porous metal substrate and the melting point temperature of the dense gas-selective membrane.

The intermediate layer may be deposited on the porous substrate by applying the same methods for depositing the materials used to form the dense gas selective membrane.

There is at least one vent over the gas tight seal between the membrane and the wall of the transfer line. This permits the separated gas to be removed from the transfer line. While a sweep gas could be used, it is not recommended as this will result in further separation or purification of the recovered stream.

In operation, the cracked gas leaves the cracker at a temperature from about 800° C. to about 950° C. and a pressure from about 100 to 110 kPa. In the transfer line, the temperature may fall as low as 450° C., but, in some embodiments, in the transfer line, the temperature is maintained at at least 500° C. The temperature of the gas separation membranes should be less than 900° C. to try to reduce coke formation on the membrane surfaces. When decoking, care should be taken not to expose the membranes to excessive temperatures which causes degradation of the transport mechanism of the membrane.

The performance of the composite gas separation modules described herein can be assessed by measuring hydrogen flux through the module during operation. For example, hydrogen flux through the composite gas separation modules, in some embodiments, is at least about 4, 10, 20, or at least about 30 $(m^3/m^2-hr)_{STP}$ at about 350° C. and with a hydrogen partial pressure difference of about 1 bar. In at least one embodiment, hydrogen flux through the composite gas separation module is at least about 33.6 $(m^3/m^2-hr)_{STP}$ at about 350° C. and with a hydrogen partial pressure difference of about 1 bar.

While hydrogen is one of the components that may be removed from a cracked gas prior to further processing, it may also be desirable to remove at least some of the methane, carbon dioxide and carbon monoxide. It may also be desirable to minimize the diffusion of ethane and ethylene through the membranes, in some embodiments, to as low as possible, and, in some instances, the concentration of ethane and ethylene in the permeate stream should be less than 10 wt %, or less than 5 wt. %, or for example less than 2 wt. %.

The off gases recovered from the transfer line may be disposed of in any number of ways. They could be fed back to the burners for the furnace to make steam (high or low pressure) or they could be sent to a flare stack.

Demonstration of Concept

On line plant analysis of cracked gas at the exit of a transfer line exchanger was as follows:

| | |
|---|---|
| H2 | 34.96 mol % |
| CH4 | 5.49 mol % |
| C2H2 | 0.24 mol % |
| C2H4 | 32.58 mol % |
| C2H6 | 23.92 mol % |
| C3s | 0.66 mol % |
| C4+ | 1.07 mol % |
| CO | 78.12 Ppm |
| CO2 | 14.93 Ppm |
| _UNKNOWNS | 1.05 mol % |

The typical conditions at the exit of a TLE are a temperature in the range from 450° C. to 500° C. and a pressure of about 101 kPa.

Concurrently, a sample of gas from a port on the exit of the cracker was passed through a stainless tube to cool it to about 450° C. to about 500° C. The pressure of the gas was about 110 kPa. The sample of the gas was separated through a ceramic frit comprising 97% alumina and about 3% MgO.

The permeate was analyzed using a gas chromatograph. The results are as follows:

| | |
|---|---|
| H2 | 39.25 mol % |
| CH4 | 6.43% mol % |
| C2H2 | 28.91 mol % |
| C2H6 | 23.05 mol % |
| C-3's | 0.73 mol % |
| C-4's | 0.70 mol % |
| CO | 0.04 mol % |
| CO2 | 0.13 mol % |

The frit was not tested for cracks and specific pore size. The test was to see what differences in the compositions of gases might be. The hydrogen concentration increased in the permeate. The test demonstrates a proof of concept.

The present disclosure provides a method to partially reduce the load of $H_2$, $CH_4$, CO and $CO_2$ exiting a transfer line of a steam cracker reducing the load on the down-stream separation train of the steam cracker.

What is claimed is:

1. A transfer line between an outlet of a steam cracking furnace and an inlet to a quench exchanger comprising:
   i) a continuous passageway of a metal having a melting temperature greater than 1000° C. having a flange at one end of the passageway adapted to cooperate with the outlet from the steam cracking furnace and a flange at the opposite end of the passageway adapted to cooperate with the inlet to the quench exchanger; one or more inserts in said passageway permitting a flow of gases through said passageway, said inserts being permeable to at least one of $H_2$, $CH_4$, CO, and $CO_2$ at temperatures from 500° C. to 900° C. and spaced from an interior wall of the passageway and sealed to the interior wall of said passageway to provide one or more gas tight chambers; and one or more ports through the metal to withdraw gases from said one or more gas tight chambers; said inserts being selected from
      a) ceramic inserts having a melting point greater than 900° C. and a porosity from 5 to 75% of pores having a size from 0.001 microns to 0.5 microns and fitting within the metal casting and
      b) metal inserts having a porosity from 5 to 75% of pores having a size from 0.001 microns to 0.5 microns;
      c) or both;
   and optionally
   ii) a membrane permeable to at least one of $H_2$, $CH_4$, CO, and $CO_2$ at temperatures from 500° C. to 900° C. on said inserts to permit the passage of at least one of $H_2$, $CH_4$, CO, and $CO_2$ there through into the gas tight chamber.

2. The transfer line according to claim 1, wherein the insert is a porous ceramic formed from oxides, dioxides, nitrides, carbides and phosphates selected from porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

3. The transfer line according to claim 1 wherein the insert is resistant to coking.

4. The transfer line according to claim 1, wherein the insert is in the shape of a cone or an island.

5. The transfer line according to claim 1, wherein the insert is a metal alloy comprising one or more of iron, nickel, titanium, chromium, aluminum, chromium, nickel and molybdenum.

6. The transfer line according to claim 1, wherein the membrane is present and has a thickness from 0.1 to 10 microns.

7. The transfer line according to claim 1, wherein the membrane is present and the membrane comprises one or more metals selected from Pd, Ta, V, Pt, Nb, and Zr.

8. The transfer line according to claim 7, wherein the membrane further comprises one or more metal oxide ceramic selected from $Al_2O_3$, $BaTiO_3$, $SrTiO_3$ and $ZrO_2$.

9. The transfer line according to claim 8, wherein the membrane is a dense metal oxide membrane.

10. The transfer line according to claim 9, wherein in the membrane the metal comprises Pd.

11. The transfer line according to claim 10, wherein the metal oxide comprises yttria stabilized $ZrO_2$.

12. The transfer line according to claim 10, wherein the metal oxide comprises calcia stabilized $ZrO_2$.

13. The transfer line according to claim 9, wherein the membrane is not less than about 95% of theoretical density.

14. The transfer line according to claim 8, wherein the membrane is coated on component a).

15. The transfer line according to claim 14, wherein component a) comprises an alumina ceramic.

16. The transfer line according to claim 8, wherein the membrane is coated on component b).

17. The transfer line according to claim 8, wherein intermediate the ceramic oxide and component b) is a ceramic comprising one or more particles selected from tungsten, alumina oxide, zirconia, titania, silicon carbide, chromium oxide, yttrium oxide, having a particles size from 0.01 to 5 microns.

18. The transfer line according to claim 1, wherein the membrane is Si/C/N ceramic formed by:
   combining a monomeric and/or oligomeric silazane ceramic precursor with a comonomer comprising one or more of the group consisting of ene (vinyl) functionalized, oligomeric, inorganic or organic silazanes, difunctional thiols, and tetrafunctional thiols;
   forming the combination as a thin film on a substrate;
   photopolymerizing the thin film; and
   pyrolyzing the photopolymerized thin film so as to result in a ceramic membrane that contains substantially no oxide.

19. The transfer line according to claim 18, wherein said monomeric and/or oligomeric silazanes contain heteroatoms selected from boron, titanium, aluminum, phosphorus, and combinations thereof.

20. A cracking furnace and quench system for cracked gases comprising intermediate the exit of the cracking furnace and the quench system a transfer line according to claim 1.

* * * * *